(12) United States Patent
Rodstrom

(10) Patent No.: US 7,621,907 B2
(45) Date of Patent: Nov. 24, 2009

(54) IMPLANTABLE DRUG DELIVERY SYSTEM

(75) Inventor: Theron Robert Rodstrom, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 58 days.

(21) Appl. No.: 10/385,791

(22) Filed: Mar. 11, 2003

(65) Prior Publication Data

US 2003/0176854 A1 Sep. 18, 2003

Related U.S. Application Data

(60) Provisional application No. 60/363,150, filed on Mar. 11, 2002.

(51) Int. Cl.
*A61K 9/22* (2006.01)
(52) U.S. Cl. .................................................. 604/892.1
(58) Field of Classification Search ............ 604/890.1, 604/891.1, 892.1, 93.01
See application file for complete search history.

(56) References Cited

U.S. PATENT DOCUMENTS

| | | | |
|---|---|---|---|
| 3,416,530 A | 12/1968 | Ness | 128/260 |
| 3,432,592 A | 3/1969 | Speiser et al. | 424/19 |
| 3,828,777 A | 8/1974 | Ness | 128/260 |
| 3,845,770 A | 11/1974 | Theeuwes et al. | 128/260 |
| 3,916,899 A | 11/1975 | Theeuwes et al. | 128/260 |
| 3,921,632 A | 11/1975 | Bardani | 128/217 |
| 4,008,864 A | 2/1977 | Torphammar et al. | 242/107.4 R |
| 4,034,756 A * | 7/1977 | Higuchi et al. | 604/892.1 |
| 4,063,064 A | 12/1977 | Saunders et al. | 219/121 L |
| 4,088,864 A | 5/1978 | Theeuwes et al. | 219/121 LM |
| 4,144,317 A | 3/1979 | Higuchi et al. | 424/21 |
| 4,200,098 A | 4/1980 | Ayer et al. | 128/260 |
| 4,201,210 A | 5/1980 | Hughes et al. | 128/260 |
| 4,220,153 A * | 9/1980 | Dresback | 424/438 |
| 4,285,987 A | 8/1981 | Ayer et al. | 427/3 |
| 4,300,557 A | 11/1981 | Refojo et al. | 128/260 |
| 4,304,765 A | 12/1981 | Shell et al. | 424/14 |
| 4,451,254 A | 5/1984 | Dinius et al. | 604/62 |
| 4,601,893 A | 7/1986 | Cardinal | 424/15 |
| 4,668,506 A | 5/1987 | Bawa | 424/429 |
| 4,687,660 A | 8/1987 | Baker et al. | 424/465 |
| 4,801,460 A | 1/1989 | Goertz et al. | 424/465 |

(Continued)

FOREIGN PATENT DOCUMENTS

EP 1 347 741 B1 1/2009

(Continued)

OTHER PUBLICATIONS http://www.medscape.com—"Biocapsule May Offer New Insulin Delivery System" (Nov. 7, 2001).

(Continued)

*Primary Examiner*—Kevin C Sirmons
*Assistant Examiner*—Elizabeth R Moulton
(74) *Attorney, Agent, or Firm*—Scott A. Chapple

(57) ABSTRACT

An implantable medicament delivery device includes a core body which further includes a single basin or multiple smaller basins for containing a drug or a medicament. Each basin is covered by a screen. The implantable drug delivery device is placed within the body of an animal, and the drug is allowed to diffuse through the holes in the screen to provide treatment of a disease or condition.

13 Claims, 14 Drawing Sheets

U.S. PATENT DOCUMENTS

| | | | |
|---|---|---|---|
| 4,806,337 A | 2/1989 | Snipes et al. | 71/65 |
| 4,853,224 A | 8/1989 | Wong | 424/427 |
| 4,959,217 A | 9/1990 | Sanders et al. | 424/473 |
| 4,997,652 A | 3/1991 | Wong | 424/428 |
| 5,004,601 A | 4/1991 | Snipes | 424/78 |
| 5,004,614 A | 4/1991 | Staniforth | 424/466 |
| 5,006,342 A | 4/1991 | Cleary et al. | 424/445 |
| 5,082,655 A | 1/1992 | Snipes et al. | 424/386 |
| 5,128,145 A * | 7/1992 | Edgren et al. | 604/892.1 |
| 5,164,188 A | 11/1992 | Wong | 424/428 |
| 5,314,471 A | 5/1994 | Brauker et al. | 623/11 |
| 5,476,511 A | 12/1995 | Gwon et al. | 623/4 |
| 5,516,522 A | 5/1996 | Peyman et al. | 424/426 |
| 5,582,838 A | 12/1996 | Roark et al. | 424/472 |
| 5,660,847 A | 8/1997 | Magruder et al. | 424/424 |
| 5,693,335 A | 12/1997 | Xia et al. | 424/448 |
| 5,770,076 A | 6/1998 | Chu et al. | 210/490 |
| 5,797,898 A | 8/1998 | Santini, Jr. et al. | 604/890 |
| 5,798,042 A | 8/1998 | Chu et al. | 210/490 |
| 5,824,072 A | 10/1998 | Wong | 623/4 |
| 5,824,074 A | 10/1998 | Koch | 623/6 |
| 5,836,935 A | 11/1998 | Ashton et al. | |
| 5,869,079 A | 2/1999 | Wong et al. | 424/426 |
| 5,882,682 A | 3/1999 | Rork et al. | 424/473 |
| 5,893,974 A | 4/1999 | Keller et al. | 210/483 |
| 5,902,598 A * | 5/1999 | Chen et al. | 604/892.1 |
| 5,938,923 A | 8/1999 | Tu et al. | 210/490 |
| 5,972,369 A | 10/1999 | Roorda et al. | 424/424 |
| 5,985,328 A | 11/1999 | Chu et al. | 424/489 |
| 6,044,981 A | 4/2000 | Chu et al. | 210/490 |
| 6,107,102 A | 8/2000 | Ferrari | 436/518 |
| 6,251,090 B1 | 6/2001 | Avery et al. | 604/9 |
| 6,331,313 B1 | 12/2001 | Wong et al. | 424/427 |
| 6,740,077 B1 * | 5/2004 | Brandau et al. | 604/892.1 |
| 2002/0086051 A1 | 7/2002 | Viscasillas | 424/451 |
| 2002/0188282 A1 | 12/2002 | Greenberg | 604/890.1 |
| 2004/0180075 A1 | 9/2004 | Robinson et al. | |

FOREIGN PATENT DOCUMENTS

| | | |
|---|---|---|
| WO | WO 94/18956 | 9/1994 |
| WO | WO 97/11655 | 4/1997 |
| WO | WO 98/00107 | 1/1998 |
| WO | WO 99/11244 | 3/1999 |
| WO | WO 00/62760 | 10/2000 |
| WO | WO 01/80825 A2 | 1/2001 |
| WO | WO 02/055058 A2 | 7/2002 |
| WO | WO 03/020172 A1 | 3/2003 |

OTHER PUBLICATIONS

Press Release—National Science Foundation PR 01-87, Oct. 30, 2001—"Biocapsule Can Provide Steady Insulin Supply; Potential Breakthrough for Diabetes Patients".

http://192.148.246.31—"Intelligent Micro-Engineered Drug Delivery—Summary" by Carl F. Grove, iMEDD, Inc. (Apr. 2000).

"Technology Opportunity: Micro- and Nanotechnologies for Medical Therapeutics: Stealth Cell Transplantation, Implantable Enzymatic Reactor, Drug Delivery", National Aeronautics and Space Administration.

"Microsystem for Controlled, Continuous Drug Delivery", National Aeronautics and Space Administration (May 2002).

* cited by examiner

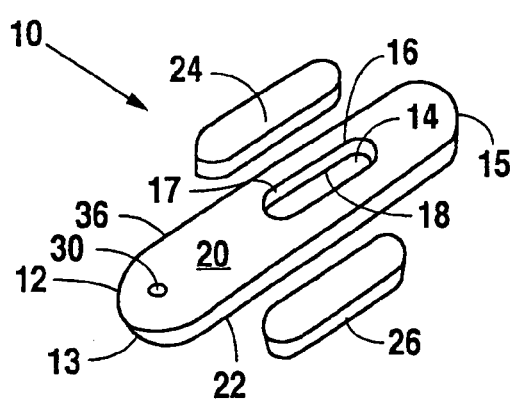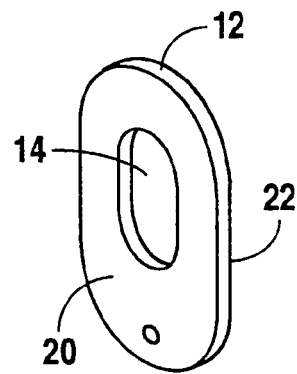
Fig. 2A                          Fig. 2B
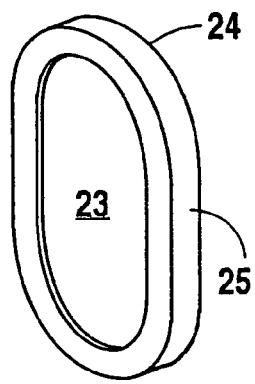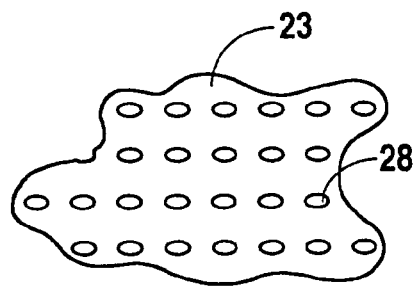
Fig. 2C                          Fig. 2D
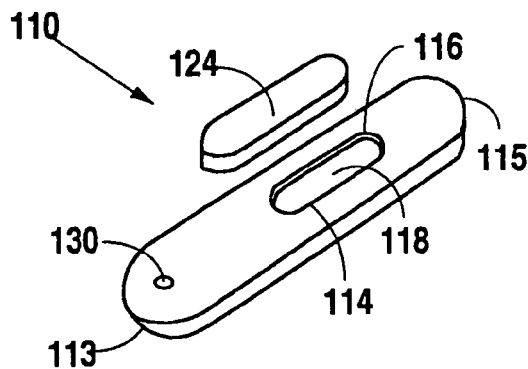
Fig. 3

IMPLANTABLE DRUG DELIVERY SYSTEM

This application claims priority from U.S. Provisional Patent Application Ser. No. 60/363,150 filed Mar. 11, 2002.

FIELD

The present invention pertains to a drug delivery system; more particularly, the present invention pertains to an implantable small drug delivery device for use with human beings or other animals.

BACKGROUND

There are many conditions or diseases which occur within the body of a human being or an animal which respond effectively to treatment by the use of one or more medicaments. For many such conditions and diseases the medicament is taken orally. Once swallowed, the medicament eventually migrates to the location of the condition or disease by passing through the gastrointestinal system. In still other instances, medicament is delivered to the location of the condition or disease through the bloodstream. Specifically, the medicament is injected by a syringe into a muscle or soft tissue and then carried by the flow of blood. In still other situations, generally in a health care facility, an IV drip may be used to place the medicament directly into a blood vessel. In yet other situations, some type of surgical intervention is used to physically place a particular medicament within the body at or near the location of a condition or disease.

It has been found that by use of the techniques developed for the creation of integrated circuits, small drug delivery devices can be manufactured which may be used to both contain and then deliver medicament to the site of a condition or disease within the human body. Examples of such small drug implantation devices are disclosed in the following U.S. patents: U.S. Pat. No. 5,770,076; U.S. Pat. No. 5,797,898; U.S. Pat. No. 5,985,328; U.S. Pat. No. 6,123,861, and U.S. Pat. No. 6,331,313. Many of these small drug implantation devices are highly complex and, accordingly, both difficult and expensive to manufacture. Thus, there remains a need in the art for a simple, low cost, easy-to-manufacture implantable small drug delivery device that can be adapted for implantation within the body of a human being or other animal to deliver medicament to a wide variety of locations.

SUMMARY

The simple, low cost, easy-to-manufacture implantable drug delivery system of the present invention enables the implantation of a mechanism within the body to deliver medicament to a wide variety of locations. The disclosed system includes at least one basin, well, or open space. The basin, well, or open space is enframed, enclosed, encased, or formed in a core body. The basin, well, or open space within the core body or basin encasement portion is of sufficient size to contain the desired amount of a medicament needed for prolonged internal treatment of a chronic condition or disease. Typical of such chronic conditions or diseases are those that are known to occur within the eye.

Covering the basin, well, or open space which is surrounded by the core body, at either the top, the bottom, or both, is a banded screen encircled by a band. The banded screen is used to control the release or movement of a drug or a medicament from a tablet, a powder, or a slurry placed in the basin, well, or open space into the body of a human or an animal. The number, size, location, and arrangement of the empty or clear holes in the banded screen or banded screens is a function of the solubility of the medicament contained in the basin, well, or open space, the dissolution rate of the medicament, the concentration of the medicament, and the form of the medicament—be it a tablet, a powder, a slurry, or a combination thereof.

Once one or more medicaments have been placed into the basin, well, or opening, and the basin, well, or opening is covered with the screen encircled by a band, the entire combination of the drug or medicament, the core body in which the basin is formed, and the banded screen is implanted within the body. For example, for conditions or diseases occurring within the eye, one technique is to insert the disclosed drug delivery system into the eye through the sclera portion. Once the disclosed drug device have been properly positioned at its desired location, it may be affixed in place using a variety of methods, to include passing sutures through a hole formed in the core body.

Dispersion of the medicament out of the basin, well, or open space occurs when fluid from the body moves through the empty or clear holes in the banded screen into the basin. This flow of fluid through the empty or clear holes in the banded screen initiates the dissolution of the medicament within the basin. The dissolved medicament will then slowly diffuse outwardly through the empty or clear holes in the banded screen to provide continuing treatment of the condition or disease as long as a quantity of medicament remains within the basin of the disclosed drug delivery device. More particularly, there is a bi-directional free flow through the holes in the banded screen both into and out of the basin. The only flow volume limiting factor is the size of the holes in the banded screen.

DESCRIPTION OF THE DRAWING FIGURES

A better understanding of the implantable drug delivery system of the present invention may be had by reference to the drawing figures, wherein:

FIG. 1A is an exploded perspective view of the preferred embodiment;

FIG. 2B is a perspective view of a core body similar to that shown in FIG. 2A;

FIG. 2C is a perspective view of a banded screen encircled by a band similar to that shown in FIG. 2A;

FIG. 2D is a magnified planar view of a portion of a screen encircled by a band such as shown in FIG. 2C.

FIG. 3 is an exploded perspective view of a first alternate embodiment;

In the following description of the preferred and alternate embodiments, reference numbers are used to facilitate the description of the disclosed invention. Throughout this description, the same numbers in the units and tens places refer to the same portion of each embodiment. The numbers in the hundreds and thousands places are used to designate an alternate embodiment.

Figure 1:
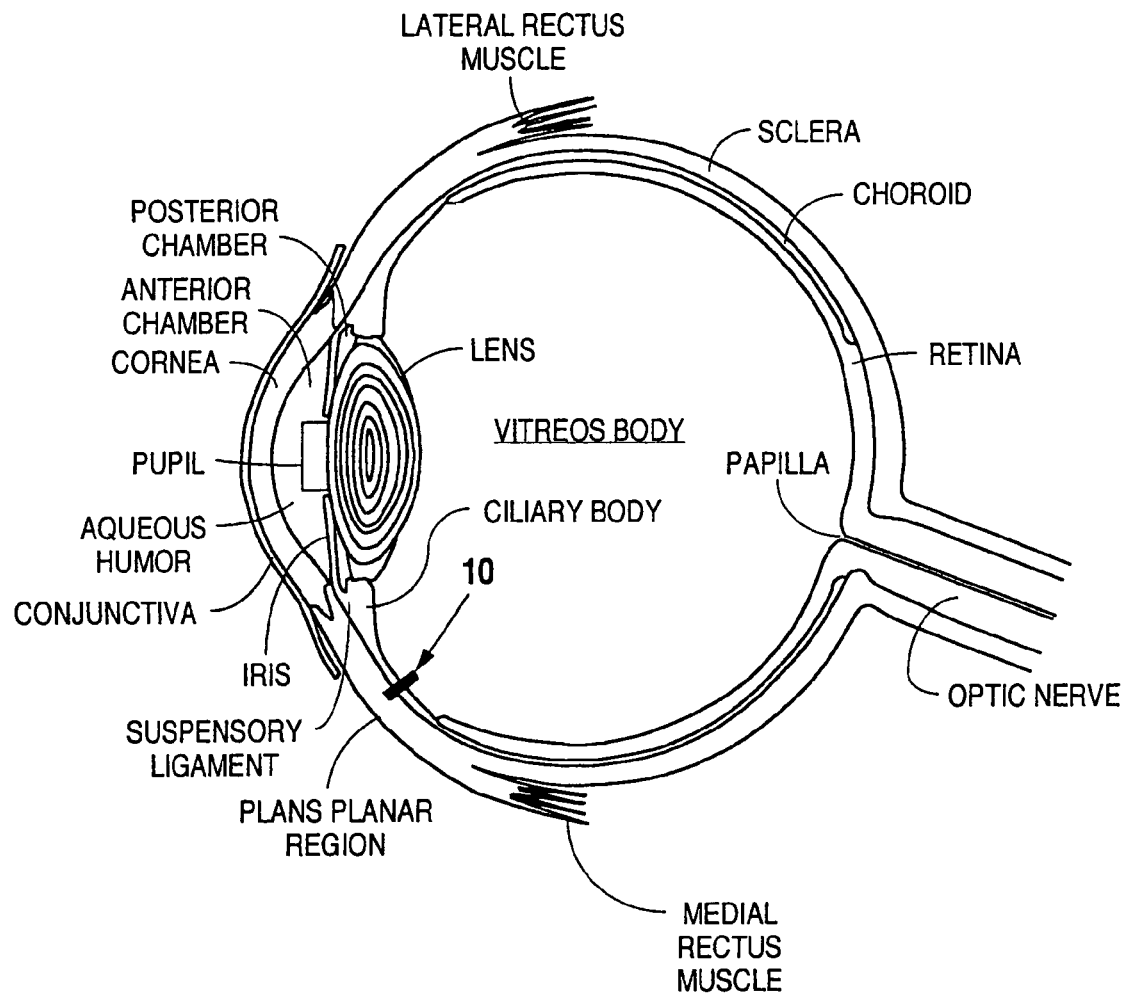
FIG. 1 is a side elevational view of an embodiment of the invention inserted into a human eye.

As may be seen in FIG. 1, the present invention is a small implantable drug delivery system 10 shown being used for the treatment of a condition or disease affecting an inner portion of the eye. Such diseases include but are not limited to ARNID (age related macular degeneration), PDR (proliferative diabetic retinopathy), neovascular glaucoma, ischemic and iatrogenic retinopathy, posterior ocular inflammation and retinal edema.

While the preferred embodiment of the present invention is described herein according to its use for treatment of inner eye diseases, it will be understood by those of ordinary skill in the art that the present invention may be used at any location in the body of an animal suitable for the treatment of a disease or condition with medicament contained in a small drug delivery device.

In addition to treatment of the diseases of the eye, the drug delivery device according to the present invention could be positioned adjacent to the prostate gland in men for the treatment of prostate cancer or benign prostate hyperplasia. By using the disclosed device, the negative side effects normally associated with the treatment of prostate cancer, such as hot flashes, vocal changes, or breast enlargement could be significantly reduced or even eliminated. In addition, those of ordinary skill in the art will understand that the amount of a drug or medicament needed for treatment of a disease or condition could be significantly reduced, thus reducing patient cost. Patient compliance with a treatment regimen would improve as the need for frequent drug administration would effectively be eliminated. Pharmacist workload and exposure to hazardous or toxic pharmaceuticals would be reduced. The opportunity for drug-drug or drug-food interaction would be effectively avoided. And, the opportunity to provide drug combination therapy would be increased.

Similar advantages could also be obtained if the disclosed device instead included a contraceptive implanted within a female. Still other potential applications include the treatment of vaginal fungal infections with an anti-fungal medicament.

Victims of Parkinson's disease would also be candidates for implantation of the disclosed drug delivery device within the brain to slowly release medicament for reduction of tremors. Patients with ulcerative colitis or a variety of different gastroenterological diseases may also be able to obtain relief by implantation of the disclosed device in their GI tract.

As may be seen in FIG. 2A, the drug delivery system 10 includes a basin 14. The basin is formed in a basin containment, enframement, or encasement portion 12. For simplification of description, the basin containment, enframement, or encasement portion is called the core body 12. In the preferred embodiment, the core body 12 is formed from a substantially planar rigid piece of material. The basin 14 in FIG. 2A is shown with a top 16 and a bottom 18. The top 16 of the basin 14 intersects the upper face 20 of the core body 12. In the preferred embodiment, the bottom 18 of the basin 14 intersects the lower face 22 of the core body 12. The illustrated basin 14 is effectively a hole which passes through the core body 12. If the top 16 is larger than the bottom 18, the basin 14 may have tapered walls 17.

A still better understanding of the construction of the core body 12 may be had by reference to FIG. 2B. Therein, the core body 12 is shown having an arcuate modified racetrack outer perimeter. The basin 14 contained therein passes completely therethrough from the upper face 20 to the lower face 22 and has a perimeter roughly parallel to the outer perimeter of the core body. For a better appreciation of the small size of the disclosed drug delivery system, the length of the core body 12 is about 9.5 mm and the width is about 5.3 mm.

The basin 14 may be located at the center of the core body 12 as shown in FIG. 2B or closer to one end of the core body 12. The size of the basin 14 is sufficient to hold a variety of different medicaments. Such medicaments may include those that are directly or indirectly a neuro-protectant, an antioxidant, an anti-apoptotic agent, a soluble growth factor agonist or antagonist, an anti-proliferative agent, an anti-angiogenic agent, an anti-edematous agent, a vascular targeting agent, an anti-inflammatory, or an antibiotic, whether they be small organic molecules or biologics, such as proteins, ribozymes, antibodies, antibody fragments, aptameters, or oligonucleotides. More specifically, suitable medicaments include, but are not limited to, signal transduction inhibitors, protein kinase antagonists, tyrosine kinase antagonists, VEGF receptor antagonists, integrin antagonists, matrix metalloproteinase inhibitors, glucocorticoids, NSAIDS, COX-1 and/or -2 inhibitors, and angiostatic steroids. Each of these medicaments may be in the form of either a powder, a slurry, or a tablet. The amount of such medicament should be sufficient to provide enough treatment of the disease for which the medicament is prescribed for a predetermined time period, depending on the type and severity of the disease. If desired, a variety of different additives may be added to the medicament to increase its effectiveness. For example, an additive with water affinity, such as an excipient humectant, may be added to the medicament for the purpose of attracting water molecules to the area where the device is inserted into the eye to initiate or to aid dissolution of the medicament or transport of the medicament out of the basin 14.

To minimize the formation of small bubbles within the basin 14, it is preferable that the size and shape of the basin 14 and the size and shape of the medicament placed in the basin 14 should be substantially the same to minimize the amount of free air.

As shown in FIG. 2C, a first screen 24 encircled by a band 25 is formed to be attached to the upper face 20 of the core body 12 to cover the top 16 of the basin 14. In the preferred embodiment, the banded screen 24 is as shown in FIG. 2C. Specifically, the banded screen 24 has an arcuate modified race track perimeter 36 which is roughly parallel to the perimeter of the basin 14 and the perimeter of the core body 12. That portion 23 of the banded screen 24 in which the holes 28 are formed may be of equal thickness with the perimeter or band portion 25 or a different thickness depending on the construction of the device 10.

As may be seen in FIG. 2D, the banded screen 24 or banded screens 24, 26 are formed to include a predetermined pattern of substantially uniform sized holes 28. The number, size, location, and arrangement of the predetermined pattern of holes 28 in the banded screen 24 or banded screens 24, 26 is a function of a variety of factors to include the solubility of the drug which is placed in the basin 14, the dissolution rate of the drug which is placed in the basin 14, and the concentration of the drug which is placed in the basin 14. Typically, the size of each individual hole in the predetermined pattern of holes 28 is controlled by the manufacturing process, such as etching, to be anywhere from substantially about 0.2 microns to substantially about 100 microns. However, because of the versatility of the disclosed invention in other applications, a still different range of substantially uniform hole sizes may be used. While it is understood that a generally uniform distribution in the predetermined pattern of the holes 28 over the surface of the banded screen 24 or banded screens 24, 26 enables maximum dissolution of the medicament, other non-uniform distributions in the predetermined pattern of holes 28 are also possible as explained below. Additionally, those of ordinary skill in the art will understand that when the drug delivery system of the present invention is used within the eye, all holes must be small enough to block the passage of any undissolved particles of medicament which might interfere with vision.

A suitable thickness for each banded screen will be from about 0.05 mm to 0.5 mm: Once the banded screen 24 is formed, the predetermined pattern of holes 28 is formed therein. A suitable thickness of the core body 12 will be from about 0.5 mm to about 3.0 mm, preferably about 1.0 mm to about 2.0 mm, depending on the amount of medicament that is intended to be administered at the target implantation site.

When either metallic or non-metallic materials are used to fabricate the disclosed drug delivery device, the banded screen 24 or banded screens 24, 26 may be affixed to the core body 12 by attaching the band portion 25 of the banded screen to the core body 12 using a variety of different adhesives, to include silicon rubber, cyano acrylates, or commonly available bio-compatible room temperature adhesives, thermal adhesives, epoxies, or ultraviolet light cured adhesives. In the preferred embodiment, the banded screen 24 or banded screens 24, 26, like the core body 12, are also formed to be substantially planar.

A variety of different materials may be used to fabricate the core body 12 and the banded screens 24, 26. Such materials may be selected from a variety of different bio-compatible materials to include silicon, glass, ruby, sapphire, diamond, or ceramic through which holes may be formed. If desired, a bio-compatible metal may be used to form the core body 12 and the banded screens 24, 26. Such bio-compatible metals include gold, silver, platinum, stainless steel, tungsten, and titanium through which holes may be formed. When a bio-compatible metal is used the band portion 25 of the banded screen 24 or banded screens 24, 26 may be welded to the core body 12 using a variety of different techniques, to include laser welding, thermo-electro bonding, as previously indicated, or the glues and adhesives described above.

Those of ordinary skill in the art will understand that the effectiveness of the disclosed drug delivery platform is determined by the delivery of the appropriate number of molecules of medicament through the predetermined pattern of holes 28 during a predetermined period of time. Accordingly, the sum total of the area of the holes 28 in the screen or screens inside the band 25 must enable the desired delivery rate of medicament from the basin 14. Generally, this is referred to as hole density. For the purposes of this disclosure, hole density is the total area of the holes divided by the total surface area of the device, even that area not covered by the holes within a banded screen.

The number of holes, their size, their location, and their general appearance on the surface of a banded screen forms the predetermined pattern of holes 28. This predetermined pattern of holes 28 will be adjusted by the physician using the disclosed invention to assure that required amount of medicament is delivered at the needed flow rate. When multiple basins are formed in the core body, multiple hole patterns in the banded screens may be used to control the flow of medicament. For example, a predetermined pattern of holes 28 having holes concentrated at one end of a basin will initially cause a fast flow of medicament. But, as the medicament is used up, the medicament will have a longer path to travel before exiting the basin 14; accordingly, the release rate of medicament out of the drug delivery basin 14 will drop off over time.

In an alternate embodiment 110 shown in FIG. 3, the bottom 118 of the basin 114 may itself be formed as a banded screen, thus obviating the need for the use and attachment of a second banded screen 26 as shown in FIG. 2A. In other applications, as shown in FIG. 3, it is also possible for the basin 114 to have a solid bottom. When the basin 114 has a solid bottom, only a single banded screen 124 is used on the top 116 of the basin 114.

Figure 4A:
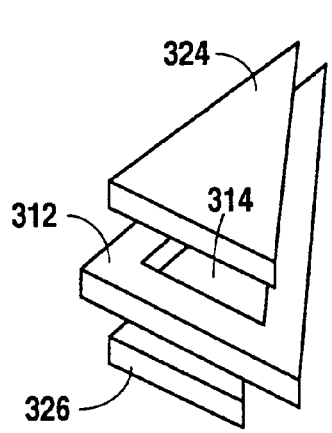
FIGS. 4A and 4B are perspective view of a first alternate embodiment.

While the preferred embodiment shows a modified racetrack perimeter 36 with the basin 14 closer to the distal end 15 and a suture hole 30 placed at the proximal end 13, it will be understood by those of ordinary skill in the art that numerous other designs of the implantable drug delivery platform are possible without departing from the scope of the present invention. For example, the drug delivery platform may be formed with multiple suture holes 30 or with straight sides such as the triangle shape 310 as shown in FIG. 4A. Alternatively, a square shape, a circular shape, a paddle shape, or any other convenient shape which may be inserted through a small incision in the eye or located in a portion of the body where the medicament is determined to be most effective may be used.

Figure 4B:
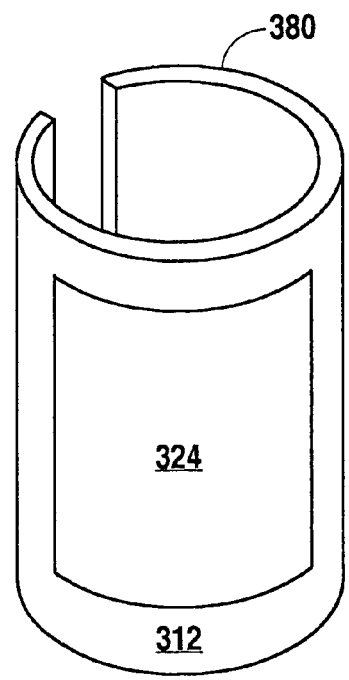

Because of the adaptability of the disclosed invention to being configured in a variety of different shapes, particularly if the core body and banded screen(s) are formed of a biocompatible metal, the disclosed device may be formed as a ring or in a cylinder 380 having a basin therein, as shown in FIG. 4B. When configured in this manner, the device may be crimped around a tendon, a ligament, a muscle fiber, a blood vessel, a nerve bundle, or any other part of the body which would respond to local administration of a medicament. Similarly, such cylinder 380 could also be placed within a tubular conduit such as an artery or a vein within the body and either expanded or sutured to affix its position.

If desired, different types of medicaments may be placed in different core bodies having different shapes or different colors. The use of different medicaments in different shaped or colored core bodies will reduce confusion of medications by enabling surgeons to distinguish between medicaments by the shape or color of the device in which the medicament is contained.

Figure 5:
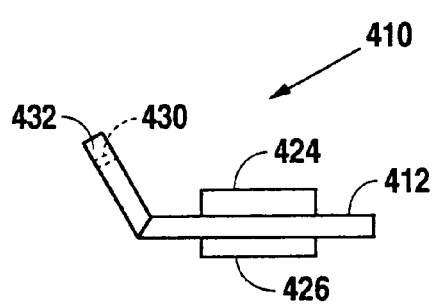
FIG. 5 is a side elevational view of the drug delivery system attached to a support piece.

In certain situations it may be necessary to orient the drug delivery device in a particular position with regard to the condition or disease being treated. In such situation, the drug delivery device 410 may be attached to a support piece 432 as shown in FIG. 5 to enable a desired orientation of the core body 412.

Figure 6A:
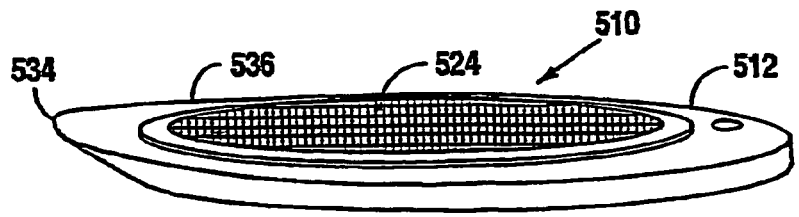
FIG. 6A is a perspective view of the drug delivery system including a sharpened edge or scalpel nose portion.
Figure 6B:
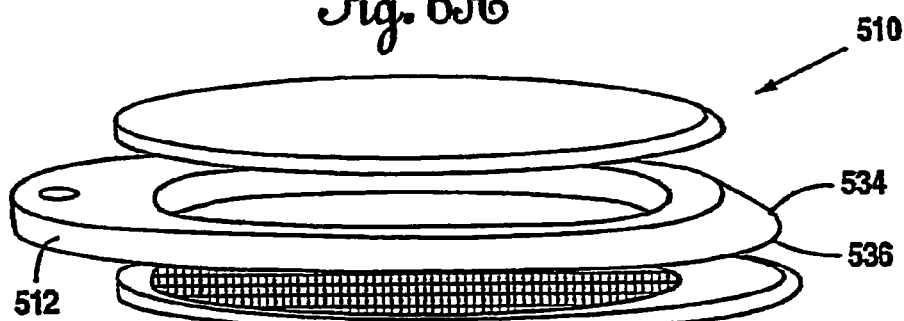
FIG. 6B is an exploded view of the embodiment shown in FIG. 6A.

In still another embodiment of the drug delivery platform 510 as shown in FIGS. 6A and 6B, the core body 512, the upper banded screen 524, and a lower plate 523 may be fabricated to form a sharpened edge 534. While a thin planar embodiment as shown in FIGS. 2A, 3 and 4A may be suitable for insertion into the vitreous body of the eye, other applications may require penetration of soft tissue. When the core body 512 is formed such that a portion of the perimeter edge 536 of the core body 512 is formed to include a sharpened edge 534, the core body 512 itself may be used to make an initial incision or enlarge an incision through which the drug delivery device 510 is placed. In this embodiment, the leading edge of the upper banded screen 524 is that portion of the sharpened edge which is used to make initial contact for creating an opening through which the disclosed drug delivery device may be inserted.

Figure 6C:
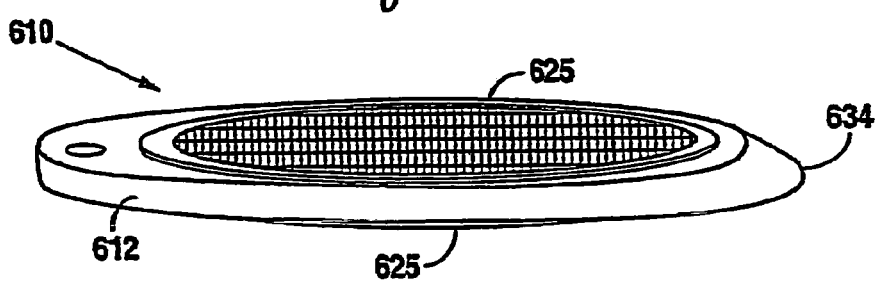
FIG. 6C is a perspective view of the drug delivery system including a sharpened edge similar to that shown in FIG. 6A.
Figure 6D:
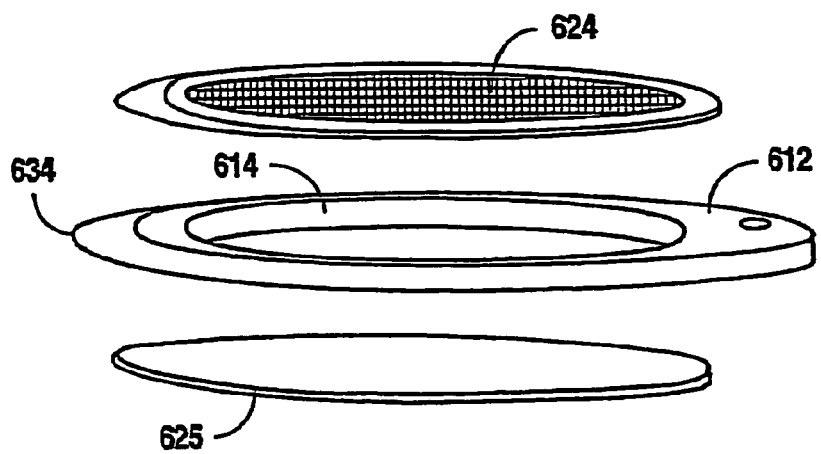
FIG. 6D is an exploded view of the embodiment shown in FIG. 6C.

In yet another alternate embodiment 610, as shown in FIGS. 6C and 6D, the sharpened edge may be placed on the portion on the edge of a solid piece 625 located under the basin 614.

Figure 7:
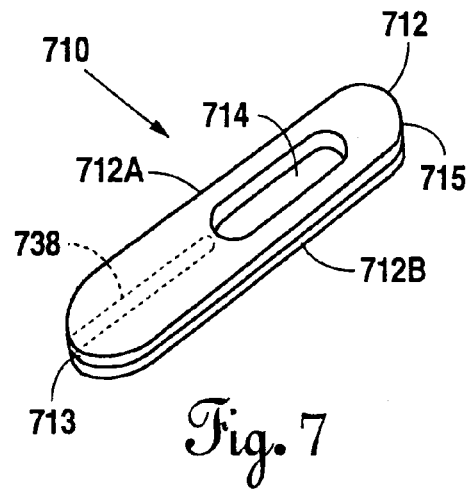
FIG. 7 is a perspective view of an alternate embodiment of the core body of the drug delivery system of the present invention further including a channel for the resupply of medicament to the basin.

While sufficient medicament can be placed within the basin of the core body to treat the condition or disease for a minimal or prolonged period of time, it may be necessary to actually replace the medicament if the condition or disease is particularly persistent. While the entire device may be replaced, it has been found that when the device is used inside a patient for a prolonged period of time, such as a year or more, the basin 714 within the core body 712 may be refilled by the use of a passageway 738 running from the perimeter edge 736 of the core body 712 into the basin 714 as shown in FIG. 7. Because of the small size of the core body 712, it may not be possible to drill a passageway from the perimeter edge 736 to the basin 714. In such cases, it may be necessary to form the core body 712 from two mating pieces 712A, 712B, each mating piece including a partial channel. These two partial channels come together either horizontally or vertically to form a small hole 738 from the perimeter edge 736 to the basin 714 when the mating pieces 712A and 712E are placed one on top of the other.

Figure 7A:
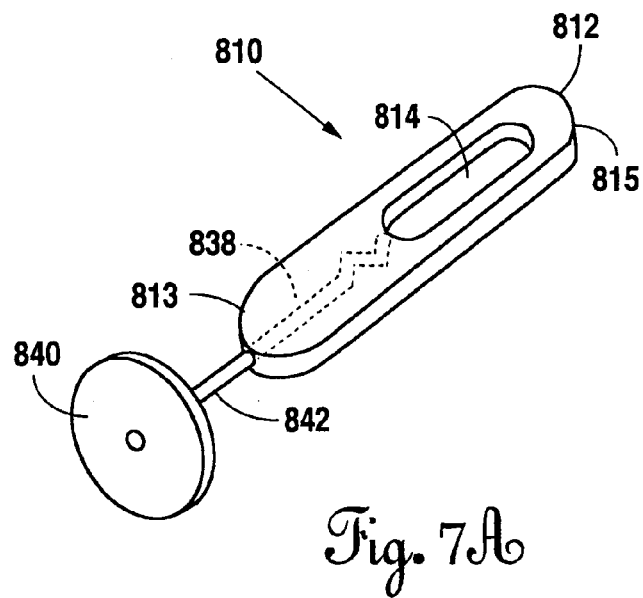
FIG. 7A is an alternate embodiment of the core body of the drug delivery system shown in FIG. 7, including a flanged portion.

In still another embodiment 810, the end of the passageway 838 may be attached to a flange 840. The flange 840 facilitates location of the opening for the refilling of the basin 814 with a medicament by the use of a syringe (not shown). In addition, the use of a flange 840 may prevent or reduce contamination. The flange 840 may be located on the side of the core body 812 or a short distance away and connected by a small tube 842. The passage way 838 may be formed as a tortuous path as shown in FIG. 7A.

Figure 8:
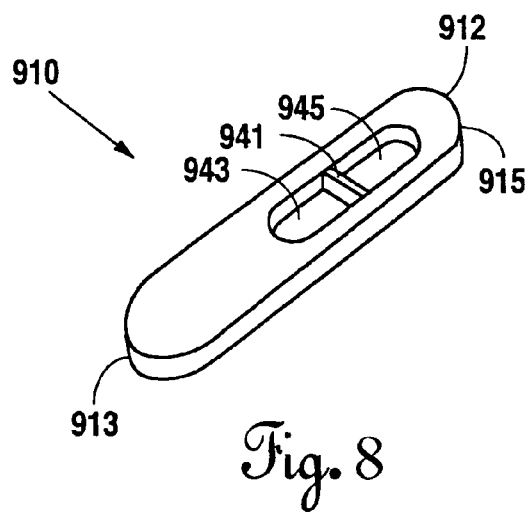
FIG. 8 is a perspective view of yet another alternate embodiment of the drug delivery system, including multiple smaller basins.

In complex situations, it may be necessary to place multiple medicaments near the site of the condition or disease. In such cases multiple basins may be formed within the core body 943, 945. As shown in FIG. 8, the core body 912 includes at least a smaller proximal basin 943 and a small distal basin 945 basins with a banded screen, including a different number and different size of holes in the predetermined pattern of holes over each of the proximal 943 and distal 945 smaller basins.

Still other embodiments of the disclosed drug delivery platform appear in FIGS. 9 through 23, as described below.

Figure 9:
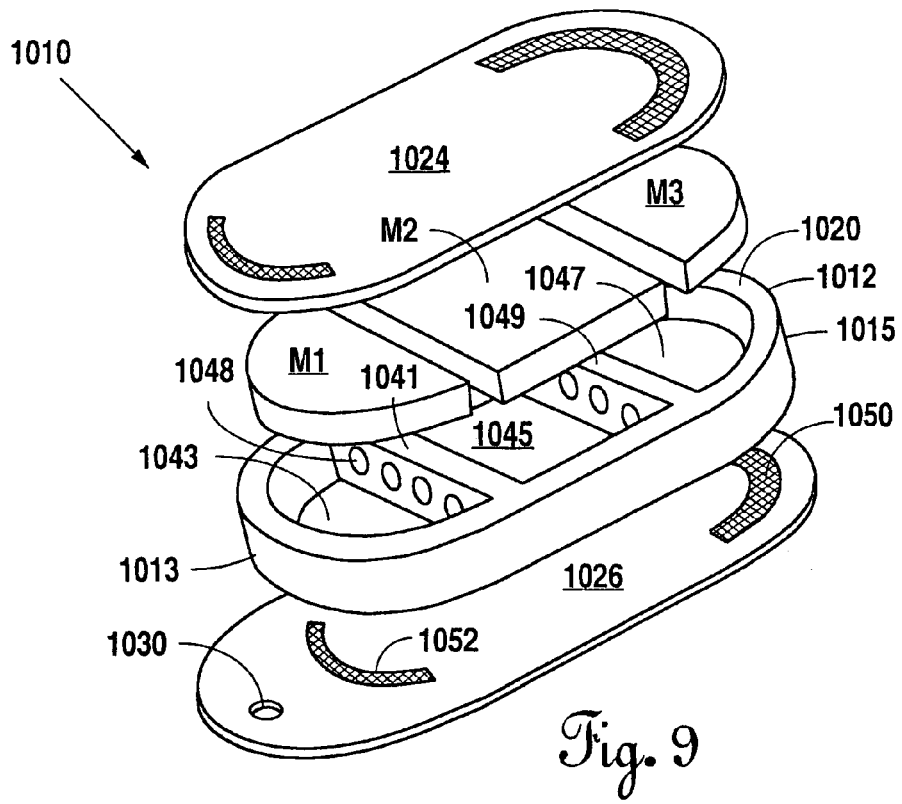
FIG. 9 is a perspective view of a drug delivery system having a three compartment basin including internal passageways for medicament migration between compartments.

In FIG. 9 is shown an embodiment of the drug delivery device 1010 which includes a proximal basin 1043, a middle basin 1045, and a distal basin 1047. The proximal basin 1043 is separated from the middle basin 1045 by use of a first partition 1041, and the middle basin 1045 is separated from the distal basin 1047 by use of a second partition 1049. If required, the transport or movement of a medicament between the various smaller basins may be facilitated by passages 1048 formed in the partitions 1041, 1049. It is also to be noted that the predetermined pattern of the holes in both the first banded screen 1024 on the upper face 1020 of the core body 1012 and the second banded screen on the lower face 1024 of the core body 1012 is formed for control of the release of medicament. Specifically, a U-shaped pattern of screen holes 1050 is included at the distal end 1015 and an arcuate pattern of screen holes 1052 is included at the proximal end 1013. This embodiment is particularly useful when it is necessary to place three medicaments, M1, M2, and M3 within the body of an animal. Alternatively, the partitions 1041 and 1049 may be solid or impermeable to keep the medicaments M1, M2 and M3 separate.

Figure 10:
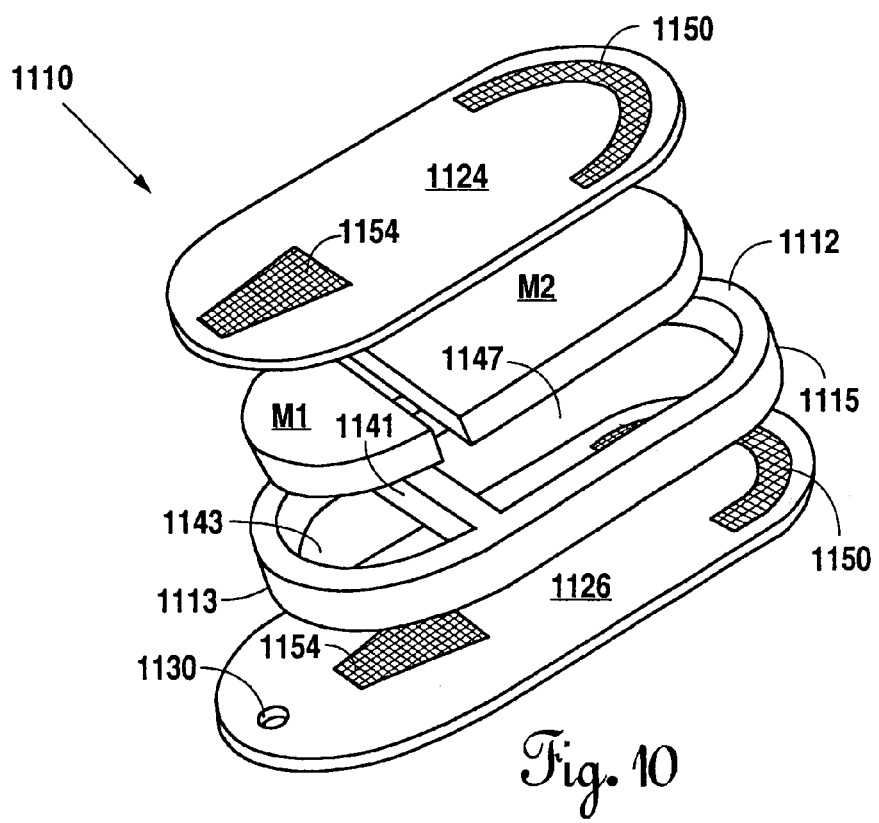
FIG. 10 is a perspective view of a drug delivery system including two smaller basin within a larger basin

FIG. 10 illustrates an embodiment 1110 for the dissipation of two medicaments, M1 and M2 within the body. Accordingly, the core body 1112 is divided into a proximal smaller basin 1143 and a distal smaller basin 1147 using a solid or impermeable partition 1141 therebetween. Release of the medication M2 is controlled by a U-shaped pattern of screen holes 1150 in both the upper banded screen 1124 and in the lower banded screen 1126 over the distal partition 1147. Over the proximal basin 1143 is located a trapezoidal pattern of screen holes 1154 for controlling the release of the medicament M1.

Figure 11:
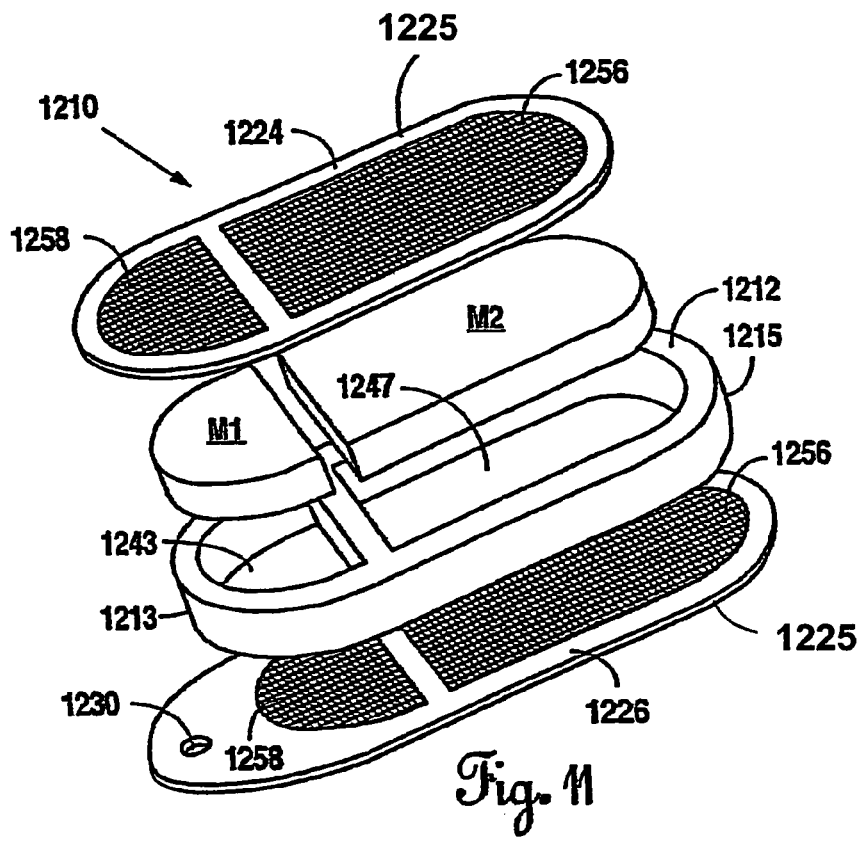
FIG. 11 is a perspective view of an alternate embodiment of the drug delivery system shown in FIG. 10.

In FIG. 11, another two-compartmented implantable drug delivery platform 1210 is shown. Note that there is a first pattern of screen holes 1256 within a band 1225 which covers the entire distal basin 1247 and a second pattern of screen holes 1258 within a band 1225 which covers the entire proximal basin 1243 which holds medicaments M2 and M1 respectively.

Figure 12:
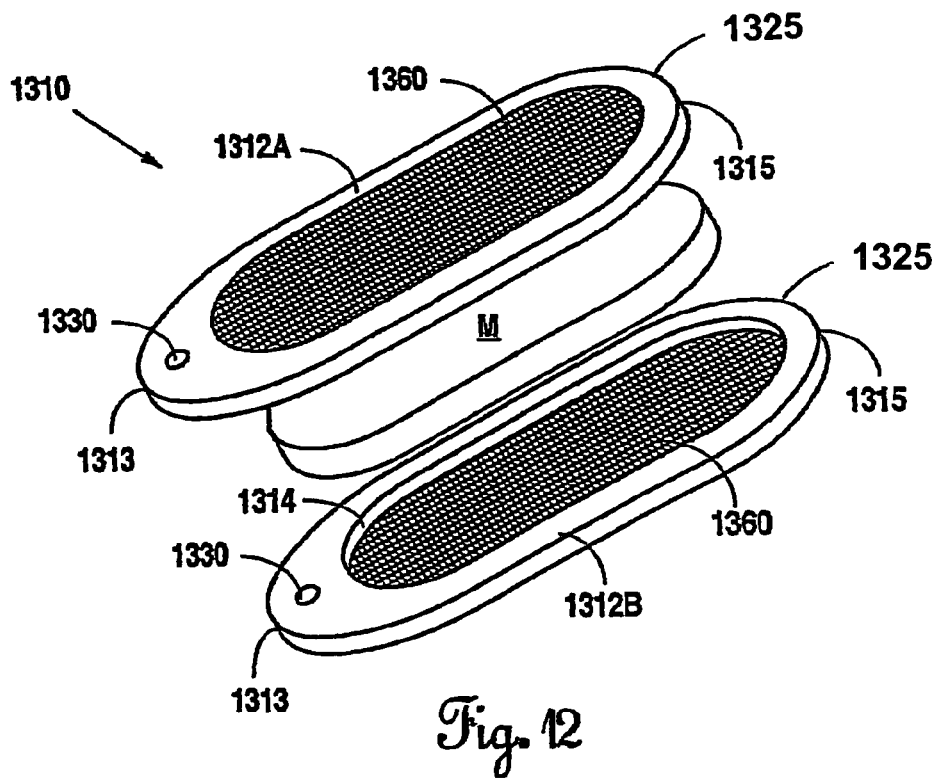
FIG. 12 is a perspective view of a drug delivery system having a single basin.

In FIG. 12 is shown an embodiment 1310 with a single basin 1314 for holding a medicament M. The single basin 1314 is formed by the joining together of the two core body pieces, 1312A and 1312B. Each of the pieces 1312A, 1312B includes a full pattern of screen holes 1360 within a band 1325 to cover the basin 1314 formed between the two portions 1312A, 1312B of the core body.

Figure 13:
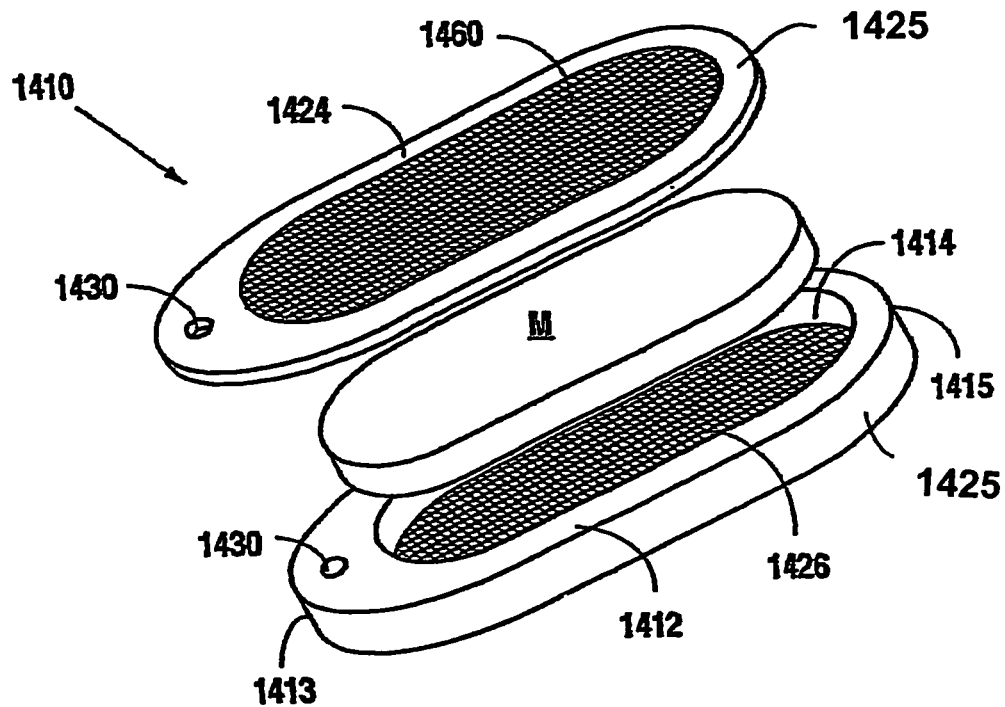
FIG. 13 is a perspective view of a first alternate embodiment of the drug delivery system shown in FIG. 12.

In FIG. 13 is shown yet another embodiment 1410 including a single basin 1414. In this embodiment 1410, the core body 1412 includes a lower banded screen 1426 covered by an upper banded screen 1424. Note that the upper banded screen 1424 fully covers the core body 1412 and is configured with a full predetermined pattern of screen holes 1460 within a band 1425 to cover the entire basin 1414.

Figure 14:
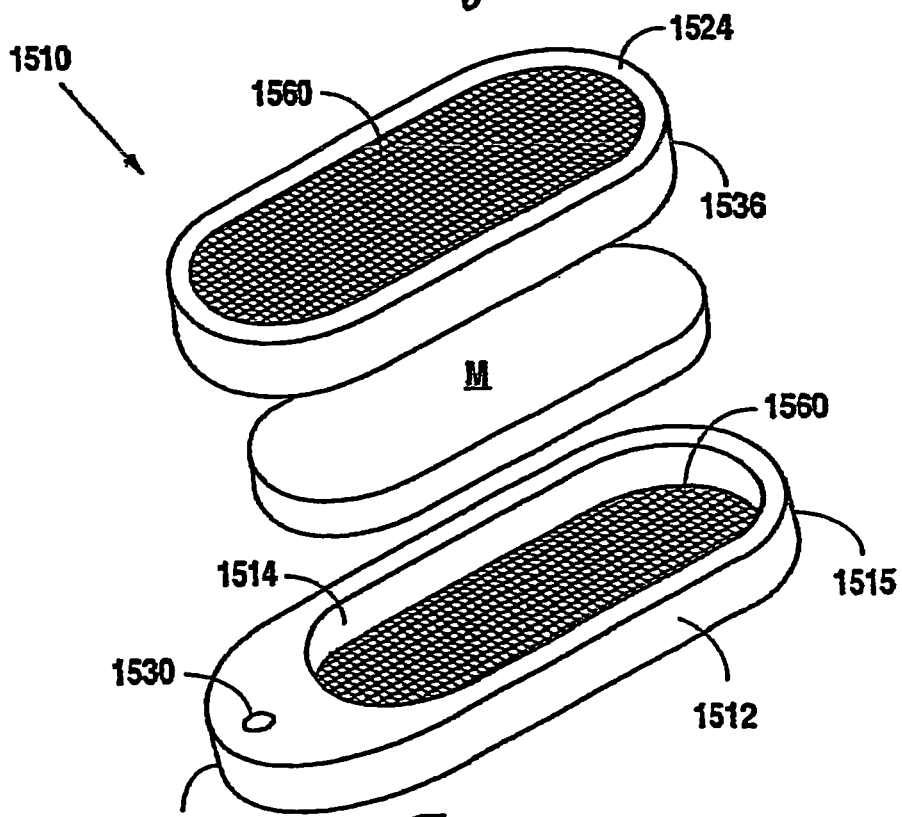
FIG. 14 is a perspective view of a second alternate embodiment of the drug delivery system shown in FIG. 12.

In FIG. 14 is shown yet another single basin embodiment 1510. In this embodiment, the upper banded screen 1524 has a perimeter 1536 extending downwardly therefrom which fits inside the inside perimeter of the basin 1514 formed in the core body 1512.

Figure 15:
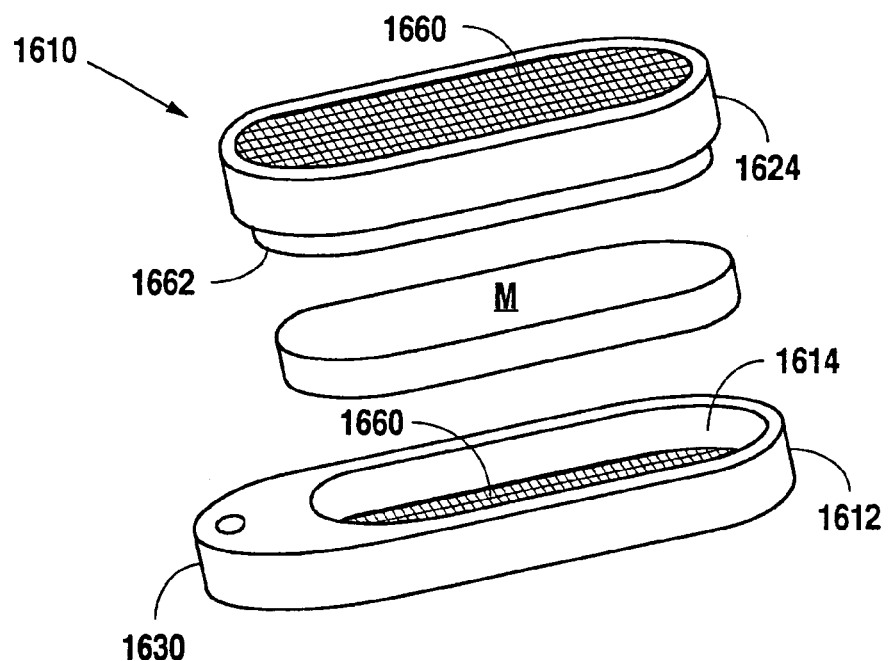
FIG. 15 is a perspective view of a third alternate embodiment of the drug delivery system shown in FIG. 12.

In FIG. 15 is shown yet another embodiment 1610 with a single well 1614. In this embodiment 1610, the upper banded screen 1634 includes a downwardly depending flange 1662 which is constructed and arranged to be press fit within the perimeter of the basin 1614 formed within the core body 1612 to extend upwardly to engage a recessed portion in a banded screen 1624.

Figure 16:
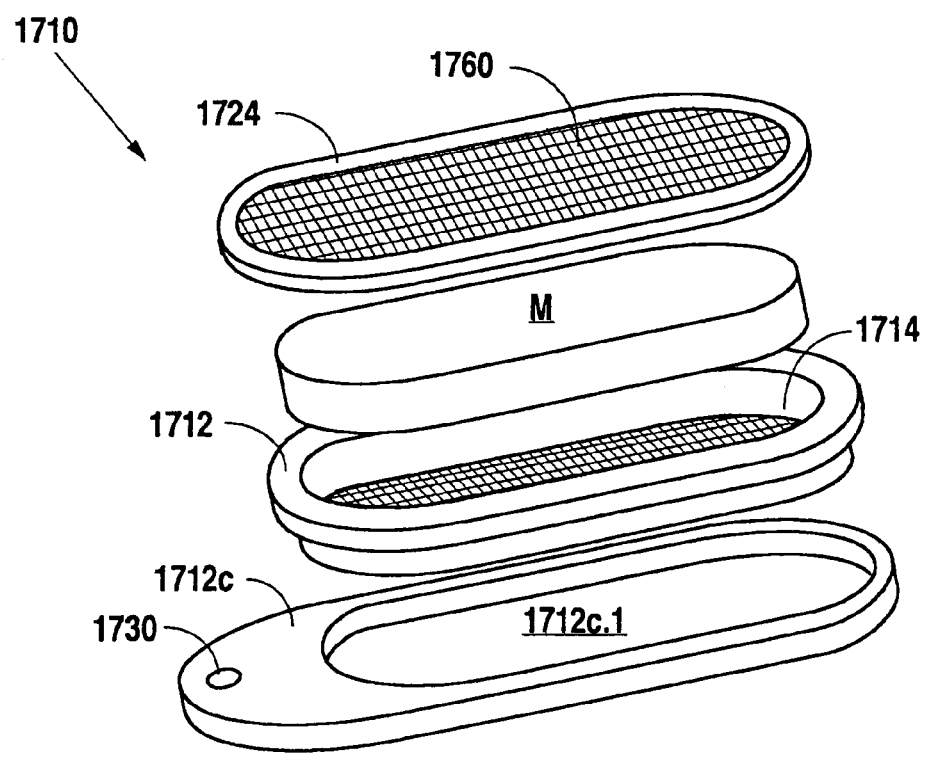
FIG. 16 is a perspective view of a fourth alternate embodiment of the drug delivery system shown in FIG. 12.

In FIG. 16 is shown yet another embodiment 1710 having a single basin 1714. The single basin 1714 is formed in a core body 1712 which further fits within a core body holder 1712C. The core body holder 1712C includes an open portion 1712C therein which will securely hold the core body 1712. Covering the basin 1714 within the core body 1712 is an upper banded screen 1724. The bottom portion of the core body 1712 is formed to be a banded screen.

Figure 17:
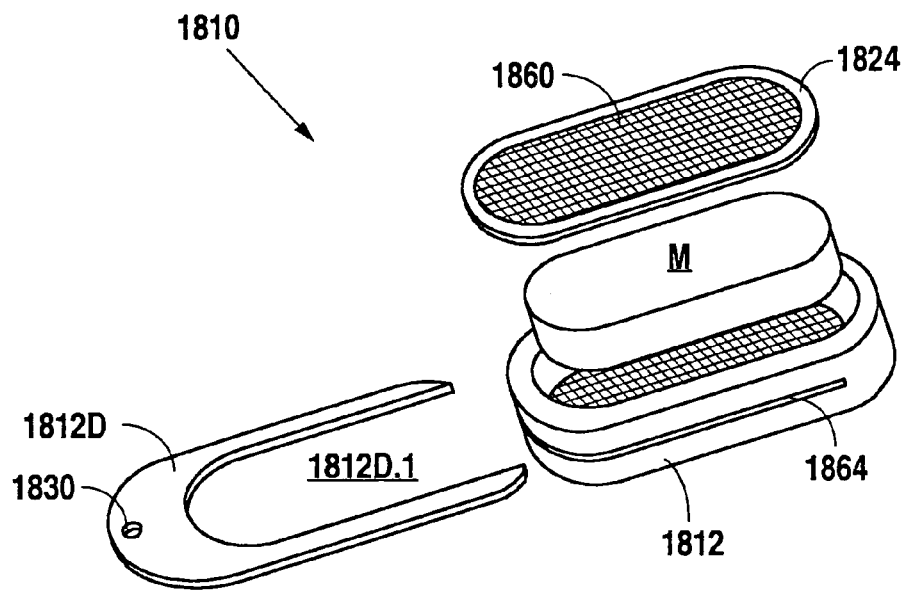
FIG. 17 is a perspective view of a fifth alternate embodiment of the drug delivery system shown in FIG. 12.

In FIG. 17 is shown an embodiment 1810 similar to the embodiment 1710 shown in FIG. 16. However, rather than the core body holder 1812D having a contiguous perimeter, the core body holder 1812D is formed to have two prongs forming an open space 1812D.1 therebetween. The open space 1812D.1 is constructed and arranged to receive the core body 1812. A groove 1864 captures the two prongs of core body holder 1812D. Once again, the core body 1812 is covered with a banded screen 1824 and the bottom of the core body 1812 is formed as a banded screen.

Figure 18:
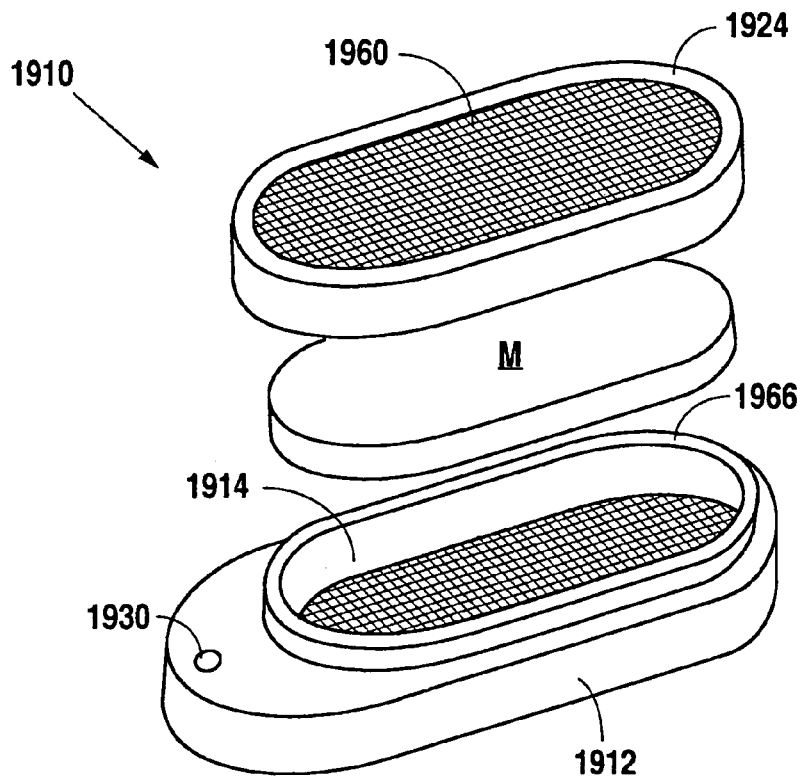
FIG. 18 is a perspective view of a sixth alternate embodiment of the drug delivery system shown in FIG. 12.

In FIG. 18 the disclosed embodiment 1910 includes a core body 1912 which has an upwardly extending flange 1966 which fits into the upper banded screen 1924 so that the upper screen 1924 may be positioned on the core body 1912 over the basin 1914.

Figure 19:
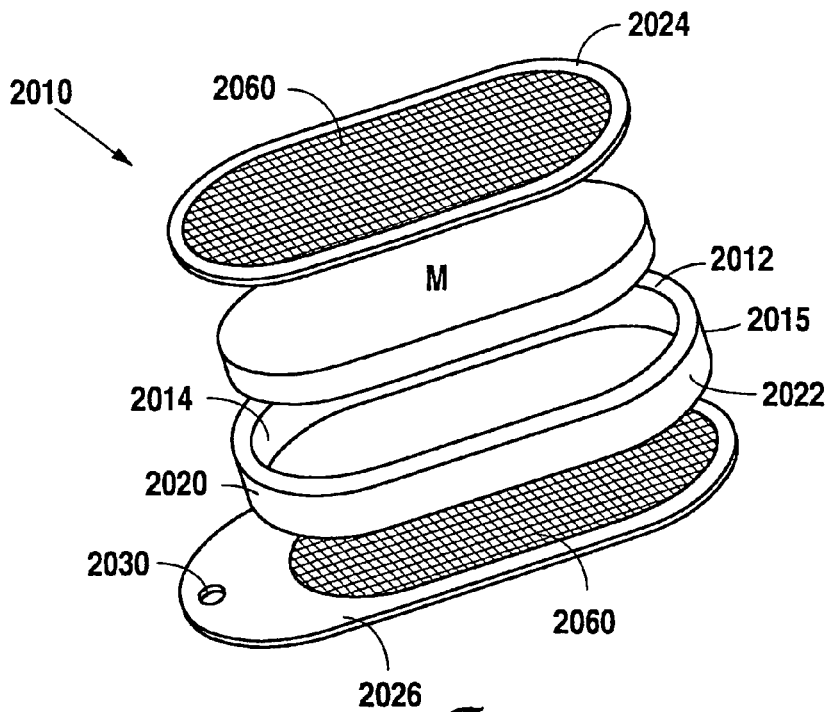
FIG. 19 is a perspective view of a seventh alternate embodiment of the drug delivery system shown in FIG. 12.

In FIG. 19 is shown an embodiment 2010 including a substantially hollow core body 2012. Resting on the bottom face 2022 of the substantially hollow core body 2012 is a lower banded screen 2026, and on the top face 2020 of the core body is an upper banded screen 2026.

Figure 20:
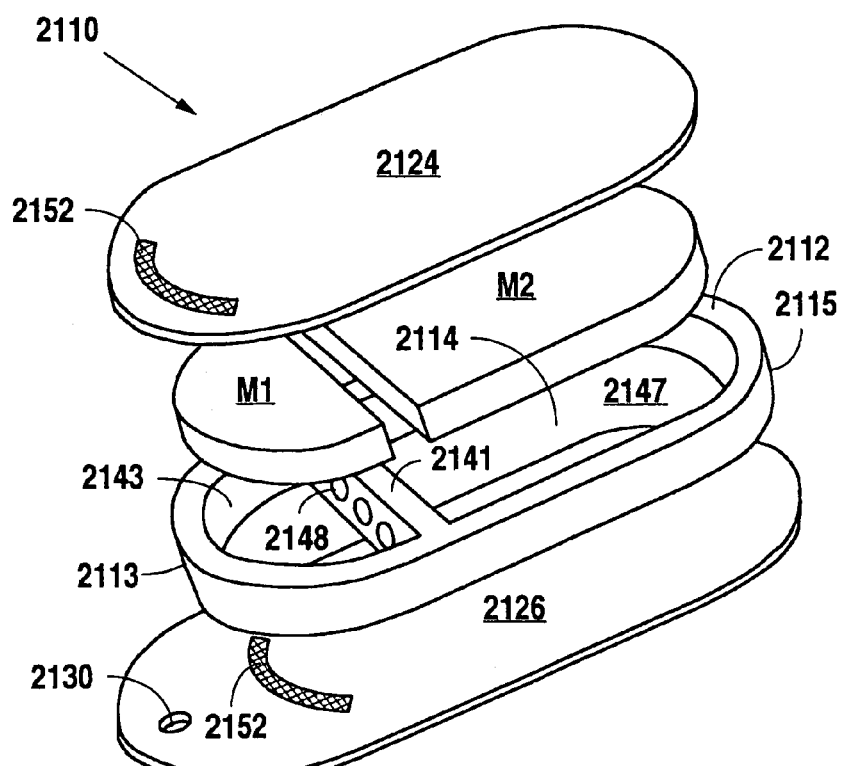
FIG. 20 is a perspective view of an eighth alternate embodiment of the drug delivery system shown in FIG. 12.

In FIG. 20 is shown an embodiment 2110 including a proximal smaller basin 2143 and a distal smaller basin 2147. The partition 2141 dividing the proximal smaller basin 2143 from the distal smaller basin 2147 has passages 2148 formed therein for the movement of medicament therethrough. Release of the medicaments M1, M2 is controlled by the predetermined arcuate pattern of holes 2152 formed in both the upper banded screen 2124 and the lower banded screen 2126. Alternatively, the partition 2141 may run along the long axis of the basin 2114 to form side-by-side smaller basins.

Figure 21:
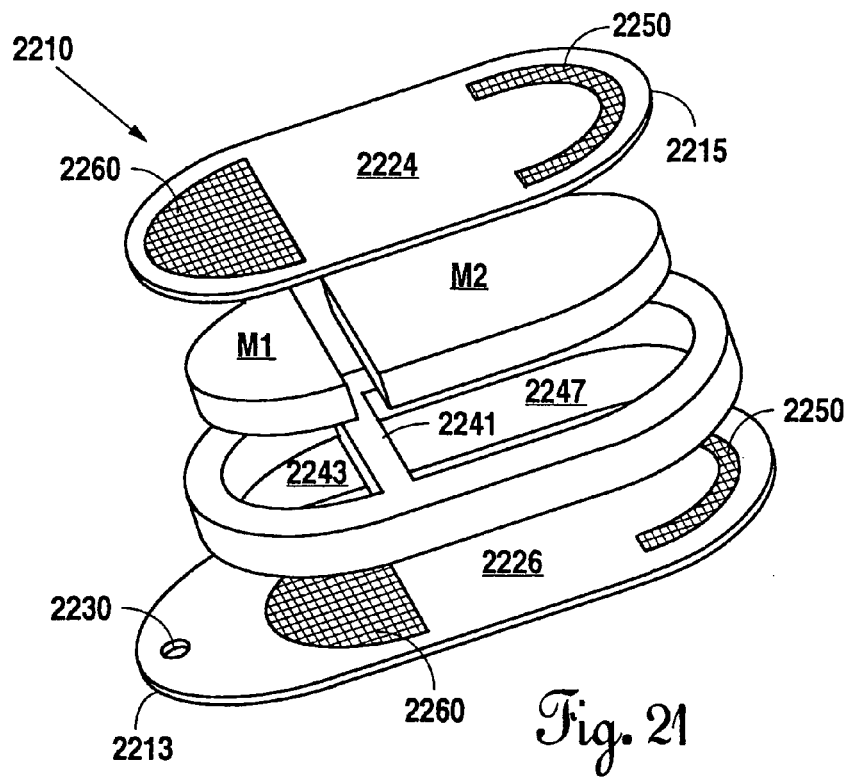
FIG. 21 is a perspective view of an first alternate embodiment of the drug delivery system shown in FIG. 10.

In FIG. 21 is still yet another embodiment 2210 including a proximal smaller basin 2243 and a distal smaller basin 2247. A partition 2241 divides the proximal basin 2243 from the distal basin 2247 in the core body 2212. Both the upper banded screen 2224 and the lower banded screen 2226 contain a U-shaped pattern of holes 2250 at the distal end 2215 and a full pattern of holes 2260 at the proximal end 2213.

Figure 22:
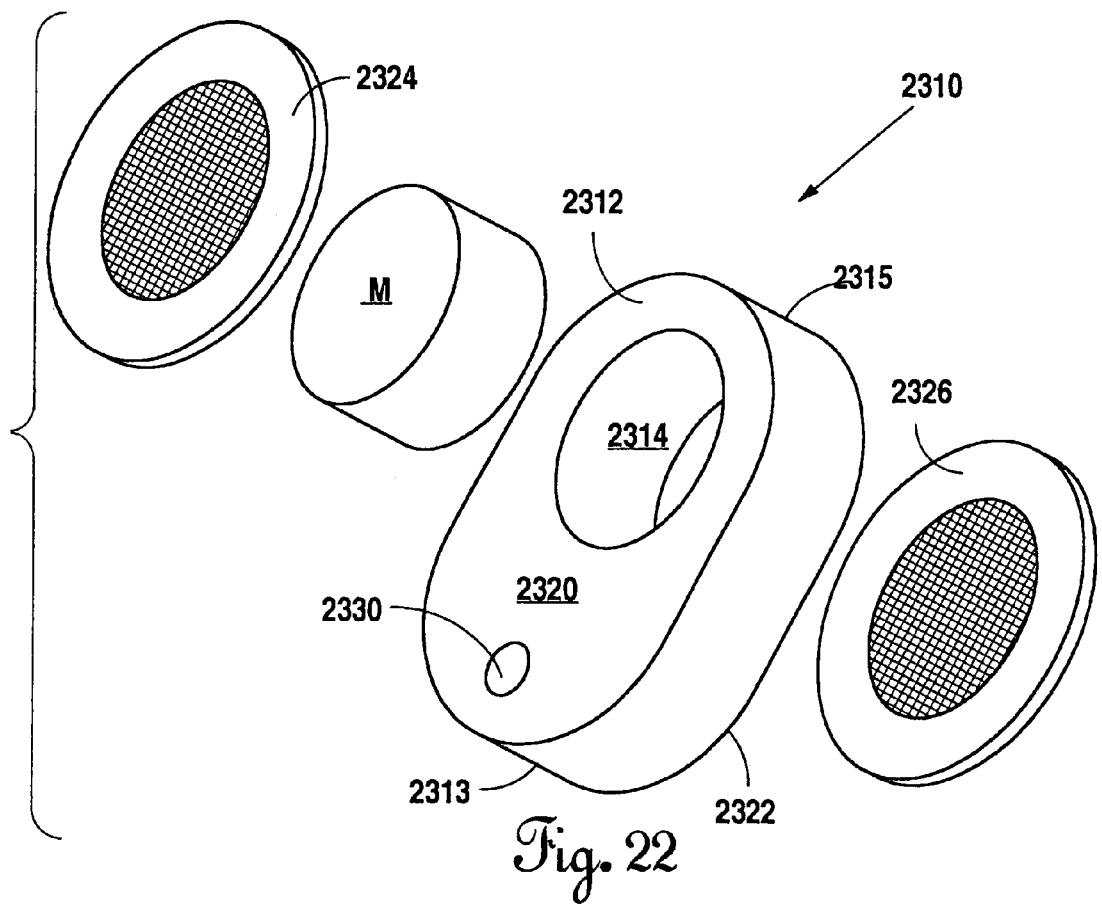
FIG. 22 is a perspective view of a second alternate embodiment of the drug delivery system shown in FIG. 10.
Figure 23:
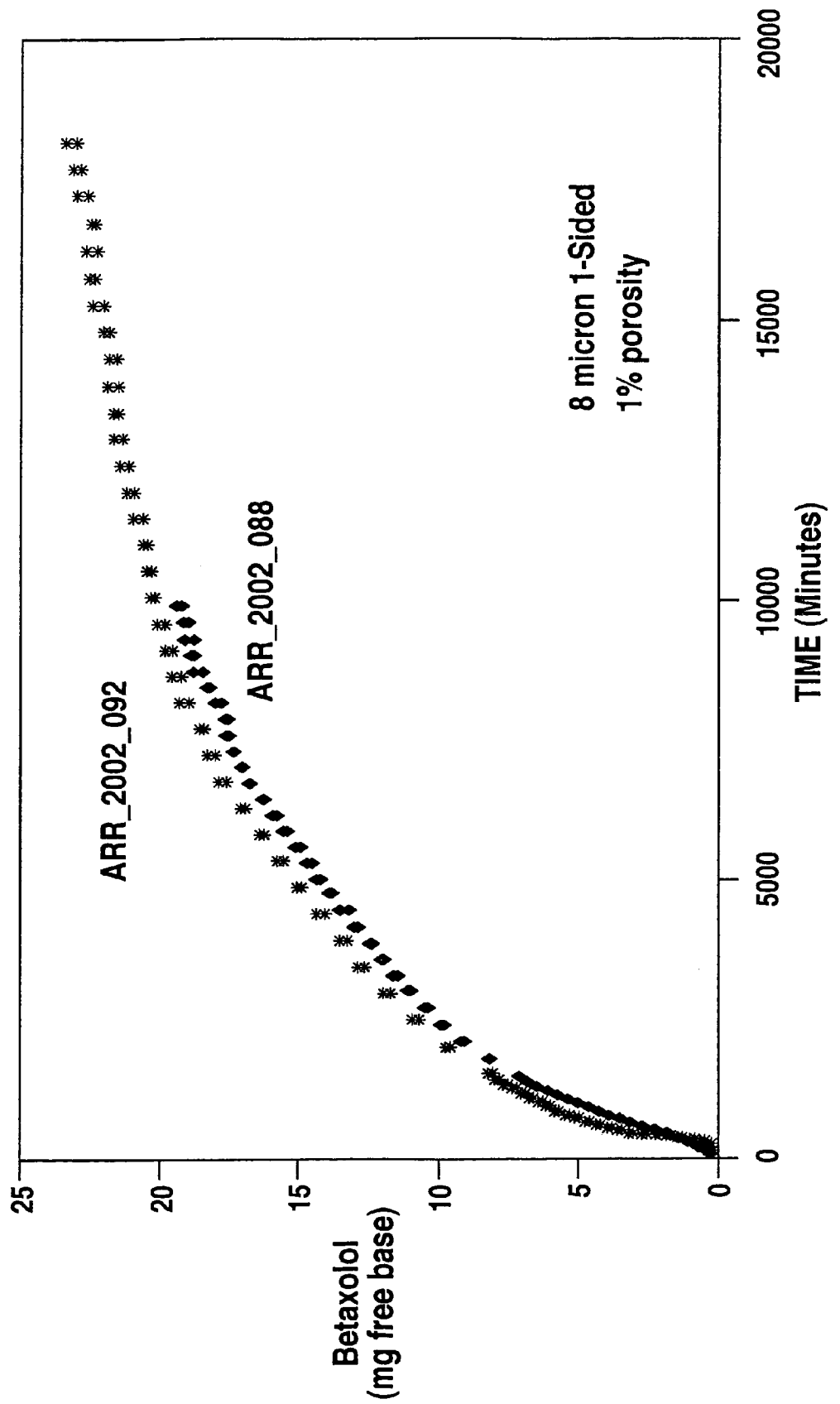
FIG. 23 is a graph of drug concentration over time in an in vitro study using betaxolol HCl tablets.

In FIG. 22 is shown an oblong thickened embodiment 2310 which includes circular banded screens 2324, 2326 to be placed on the upper face 2320 and lower face 2322 of the core body 2312.

Examples

Devices similar to those depicted in FIG. 15 were implanted into eight New Zealand White rabbits. The screen was attached to the core body using a silicone adhesive. The contralateral eye was used as a control. One rabbit was taken out of the study at two days. Three animals were tested at one month, and the remaining four rabbits were tested at three months. Histo-pathological observations were conducted at both one month and three months. At one month, three of the animals exhibited a small number of inflammatory cells in the vitreous. One animal of these three also exhibited minimal inflammation in ora serrata. The final animal had minimally swollen lens fibers. Toxicology observations for this group were unremarkable. Toxicology observations for all of the animals in the three-month sampling were unremarkable.

Figure 24:
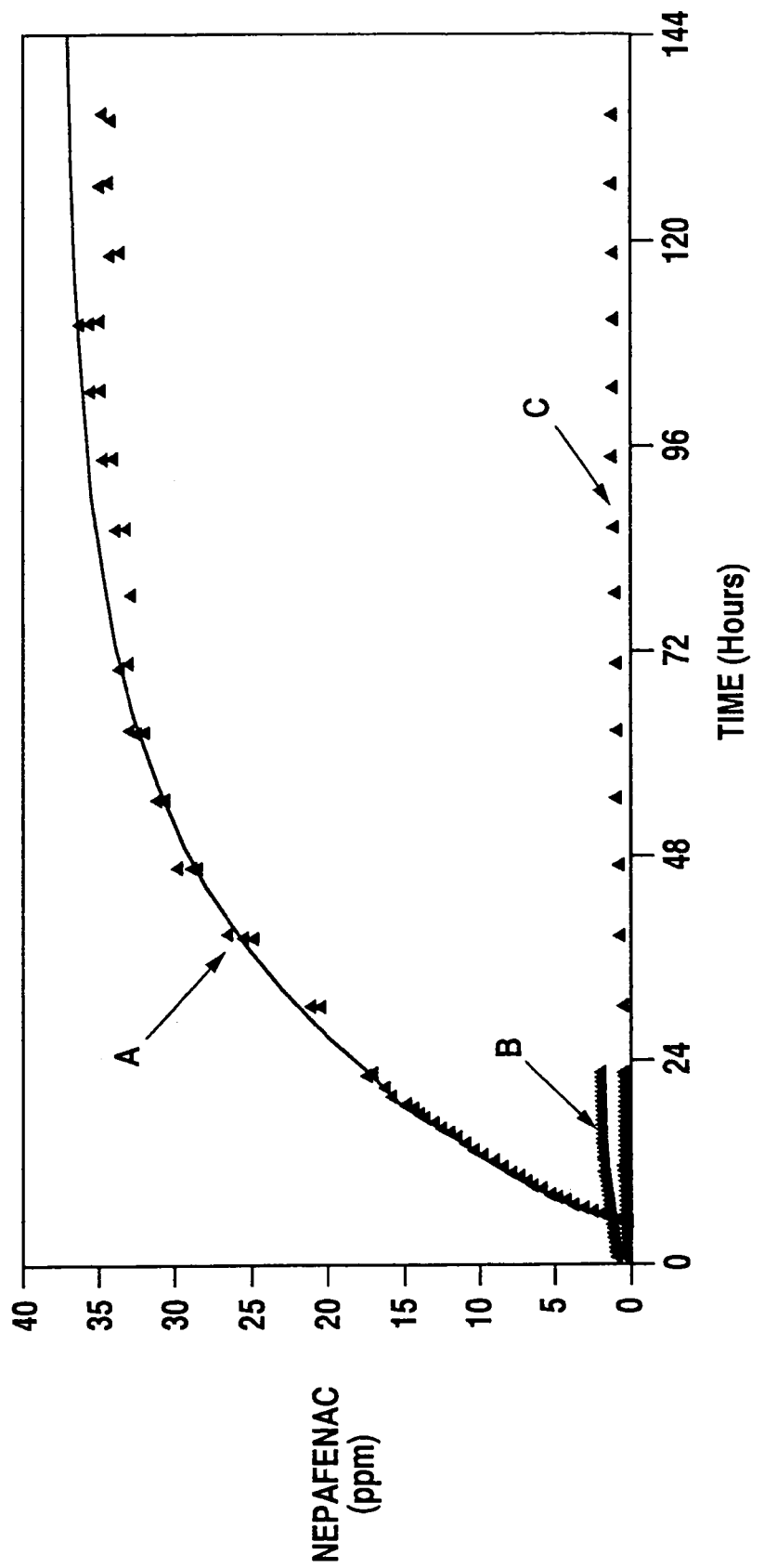
FIG. 24 is graph of drug concentration over time in an in vitro study using nepafenac tablets.

In an in vitro study, betaxolol HCl, a relatively high water soluble substance, was tableted with 10% microcrystalline cellulose and 0.40% magnesium stearate with a total weight of 22 mg. The betaxolol HCl tablet was inserted into the basin of drug delivery devices similar to the embodiment depicted in FIG. 15. The devices utilized one 8 micron 1% porosity banded screen on one side of the basin. The ratio of the area of all substantially uniform holes to the area of all surfaces on the drug delivery device was about 0.02%. Loaded drug delivery devices according to the present invention were placed in a 4 mL HPLC vial with phosphate/saline buffer and then stirred using a small stir bar. The vials were periodically sampled and analyzed for drug concentration by HPLC. As shown in FIG. 24 a plot of drug concentrates over time demonstrates the release profiles.

In a second in vitro study, another second drug formulation using a substance with a relatively low water solubility, nepafenac in tablet form, was also studied in a device similar to the embodiment depicted in FIG. 15. These tablets also contained 10% microcrystalline cellulose and 0.40% magnesium stearate. One tablet was placed in a two-sided 14 micron 25% porosity device. The ratio of the area of the area of all substantially uniform holes to the area of the banded screen was about 4.5%. The ratio of the area of all holes to the area of all surfaces on the drug delivery device was about 0.48%. A second tablet was placed in a two-sided 14 micron 1% device. The ratio of the area of all holes to the are of the banded screen was about 0.18%. The ratio of the area of all holes to the area of all surfaces on the drug delivery device was bout 0.02%. The drug release studies were performed as described above. As shown in FIG. 25, plot "A" shows the release profile from the two-sided 14 micron 25% porosity device. Plot "B" is the release profile from the two-sided 14 micron 1% porosity device. A third experiment was performed by replacing the phosphate/saline buffer from the two-sided 14 micron 1% porosity device and reinitiating the experiment. This experiment is demonstrated by plot "C."

Operation

Once a medical condition or disease within the body is identified and located, a physician will determine whether or not such condition or medication may be treated with a medicament placed in close proximity to site of the condition or disease. If the decision is made to treat the condition or disease with a medicament placed close to the condition or disease, it then becomes necessary to actually place the medicament near the condition or disease. In other applications, it may be necessary to treat a condition or disease from a short distance. Such short distance treatment may require sustained levels of medicament flow from the drug delivery device.

In the embodiment 10 shown in FIG. 1, the condition or disease is contained within the eye of a patient. For example, a surgeon may insert an implantable device into the vitreous chamber of a patient by making a small incision in the sclera. The drug delivery platform 10 is then inserted through the incision and held in place by threading a suture through the suture hole 30 in the core body 12 and attaching the other portion of the suture to the eye. The orientation of the platform is such that the implanted platform remains out of the path of light rays from the lens to the retina.

To prevent coating of the implanted devices with cells which can block the movement of medicament from the basin through the empty holes in the banded screen, an anti-proliferative coating may be used on both the screen and core body. Similarly, materials such as silicon may form chips so as to prevent chipping the banded screen, and the core body may be coated with a substance to prevent chipping.

As previously mentioned, while the preferred embodiment is shown for the purpose of inserting medicament to treat a condition or disease within the inner eye, those of ordinary skill in the art will understand that the disclosed implantable drug delivery platform 10 may be used at any location within the body of an animal where a condition or disease is best treated with an implanted medicament.

The present invention, having now been disclosed according to its preferred and alternate embodiments, will now be understood by those of ordinary skill in the art. Those of ordinary skill in the art will understand that numerous other embodiments of the present invention may also be embodied by the foregoing disclosure. Such other embodiments shall be included within the scope and meaning of the appended claims

What is claimed is:

1. An implantable medicament delivery device comprising:
    a basin constructed and arranged to contain the medicament, said basin being surrounded by a basin containment portion formed from a non-permeable material;
    one or more screens, each screen of the one or more screens including a predetermined pattern of bi-directional flow empty holes for controlling the free flow of dissolved medicament therethrough, each pattern of holes of each screen being encircled by a band constructed and arranged to cover the top or bottom of said basin when said band is affixed to said basin containment portion, each screen of the one or more screens having a thickness from about 0.05 mm to about 0.5 mm and said bi-directional flow empty holes having a size from about 0.2 microns to about 100 microns;
    wherein the bi-directional flow empty holes assure that a required amount of medicament is delivered at a needed flow rate therethrough and wherein said flow rate is based upon one or more factors selected from the group including solubility of the medicament, medicament dissolution rate and medicament concentration and wherein the bi-directional flow empty holes are the exclusive mechanism for controlling the free flow of dissolved medicament and wherein the basin is arranged to contain the medicament without containing any plunger or alternative device for aiding flow of the dissolved medicament.

2. The implantable medicament delivery device as defined in claim 1 wherein the one or more screens include at least two screens.

3. The implantable medicament delivery device as defined in claim 1 wherein said basin passes through said basin containment portion.

4. The implantable medicament delivery device as defined in claim 1 wherein said basin containment portion is substantially planar.

5. The implantable medicament delivery device as defined in claim 1 wherein said basin includes a plurality of sections separated by an impermeable barrier.

6. The implantable medicament delivery device as defined in claim 1 wherein said one or more screens are made from silicon.

7. The implantable medicament delivery device as defined in claim 2 wherein said basin is made from silicon.

8. The implantable medicament delivery device as defined in claim 2 wherein said at least two screens are made from silicon.

9. A device for delivering medicament within the body of an animal in close proximity to a condition treatable by said medicament, said device comprising:
    a basin containment portion having a first face, a second face, a perimeter, and a medicament basin between said first face and said second face of said basin containment portion being formed from a non-permeable material;
    one or more screens, each screen of the one or more screens including a predetermined pattern of bi-directional flow empty holes for controlling the release of dissolved medicament therethrough, each pattern of holes of each screen being encircled by a band, said band being affixed to said first face or said second face of said basin containment portion near the intersection of said basin respectively with said first face or said second face of said basin containment portion;
    each screen of the one or more screen having a thickness from about 0.05 mm to about 0.5 mm and said bi-directional flow empty holes having a size from about 0.2 microns to about 100 microns;
    wherein the bi-directional flow empty holes assure that a required amount of medicament is delivered at a needed flow rate therethrough and wherein said flow rate is based upon one or more factors selected from the group including solubility of the medicament, medicament dissolution rate and medicament concentration and wherein the bi-directional flow empty holes are the exclusive mechanism for controlling the free flow of dissolved medicament and wherein the basin is arranged to contain the medicament without containing any plunger or alternative device for aiding flow of the dissolved medicament.

10. The device as defined in claim 9 wherein the one or more screens include at least two screens.

11. The device as defined in claim 10 wherein said basin in said basin containment portion includes a plurality of smaller basins separated one from another by an impermeable wall.

12. The device is defined in claim 9 wherein said one or more screens are made from silicon.

13. The device is defined in claim 10 wherein said at least two screens are made from silicon.

* * * * *

UNITED STATES PATENT AND TRADEMARK OFFICE
CERTIFICATE OF CORRECTION

PATENT NO. : 7,621,907 B2  Page 1 of 1
APPLICATION NO. : 10/385791
DATED : November 24, 2009
INVENTOR(S) : Theron Robert Rodstrom It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this

Twenty-sixth Day of October, 2010

David J. Kappos
*Director of the United States Patent and Trademark Office*